United States Patent [19]

Lunn et al.

[11] 4,247,537
[45] Jan. 27, 1981

[54] BLEACHING SYSTEMS COMPRISING PERCARBONATE, PERSULFATE, AND PYROGENIC SILICA

[76] Inventors: Peter F. R. Lunn, Hoon Hay Rd., Christchurch; Joyce Grainger, 95 Dunns Ave., Kaiapoi, both of New Zealand

[21] Appl. No.: 49,803

[22] Filed: Jun. 18, 1979

Related U.S. Application Data

[63] Continuation of Ser. No. 959,148, Nov. 9, 1978, abandoned.

[30] Foreign Application Priority Data

Nov. 9, 1977 [NZ] New Zealand .................. 185654

[51] Int. Cl.³ ............... A61K 7/135; D06L 3/00; D06L 3/02
[52] U.S. Cl. ................................ 424/62; 8/111; 252/186; 424/DIG. 3
[58] Field of Search ............... 424/62, DIG. 3; 252/186; 8/111, 111.5

[56] References Cited

U.S. PATENT DOCUMENTS

| B 464,593 | 3/1976 | Knohl et al. | 424/62 |
|---|---|---|---|
| 1,894,277 | 1/1933 | Manahan et al. | 8/111 |
| 1,986,672 | 1/1935 | Bergman | 8/111 |
| 2,254,434 | 9/1941 | Lind et al. | 252/95 |
| 2,371,545 | 3/1945 | Riggs et al. | 252/550 |
| 2,914,374 | 11/1959 | Harris et al. | 8/111 |
| 2,927,082 | 3/1960 | Young | 252/186 |
| 3,337,466 | 8/1967 | Puetzer et al. | 252/186 |
| 3,378,444 | 4/1968 | Swanson | 424/62 |
| 3,651,931 | 3/1972 | Hsiung | 8/111 |
| 3,679,102 | 7/1972 | Charle et al. | 424/62 |
| 3,819,828 | 6/1974 | McCoy | 424/62 |
| 3,823,231 | 7/1974 | Bucaria | 424/62 |
| 3,931,912 | 1/1976 | Hsiung | 8/111 |
| 3,961,634 | 6/1976 | Busch | 424/62 |
| 4,008,167 | 2/1977 | Nakagawa et al. | 252/103 |
| 4,016,090 | 4/1977 | Nakagawa et al. | 8/111 |
| 4,025,609 | 3/1977 | Matsunaga | 8/107 |
| 4,075,116 | 2/1978 | Mesaros | 8/111 |
| 4,096,240 | 6/1978 | Mathur | 424/62 |
| 4,178,351 | 12/1979 | Klebe et al. | 252/186 |

FOREIGN PATENT DOCUMENTS

859276 1/1961 United Kingdom ............... 424/62

*Primary Examiner*—Joseph L. Schofer
*Assistant Examiner*—Herbert J. Lilling
*Attorney, Agent, or Firm*—Holman & Stern

[57] ABSTRACT

The invention relates to a bleaching powder which comprises at least 25% by weight of ammonium persulphate, at least 25% by weight of sodium percarbonate or potassium percarbonate and pyrogenic silica in percentages whereby the same can in a vaporproof enclosure be marketed in a premixed dry form which is capable upon aqueous activation of bleaching hair or keratinuous fiber. The one component bleach preferably includes pyrogenic silica in the range of from 4 to 10% by weight and preferably the percentage of the persulphate and percarbonate compounds is in the range of 35% by weight each upwards. Ideally the mixture also includes sequestering and wetting agents. In other forms the invention consists in methods of bleaching and methods of preparation of the bleaching powder.

16 Claims, No Drawings

BLEACHING SYSTEMS COMPRISING PERCARBONATE, PERSULFATE, AND PYROGENIC SILICA

CROSS REFERENCES TO RELATED APPLICATIONS

This application is a continuation in part of our U.S. Ser. No. 959,148 filed Nov. 9, 1978, which is now abandoned.

BACKGROUND OF THE INVENTION

1. Field of the Invention

The invention relates to bleaching compositions and in particular to relatively stable powder compositions capable of generating a water activatable wet bleaching composition. The powder can be marketed in its dry form and exhibit a significant shelf life whereupon quantities can, when desired, be water activated for use either for the bleaching of human hair or for animal hair marking procedures during the period of activation resulting from the aqueous contact.

2. Description of the Prior Art

The use of hydrogen peroxide or other peroxide compositions as a bleaching agent especially in the presence of ammonia has long been known. Hydrogen peroxide however does have many disadvantages of which poor shelf life and difficulty of storage are the most important. Moreover when the same is used with human hair there is also a tendency for persons with sensitive scalps to be irritated by such use of hydrogen peroxide. Systems have, therefore, been devised whereby activating compounds such as persulphates, percarbonates or perborates have been added to obtain the same degree of bleaching but with a reduced concentration or amount of hydrogen peroxide. In any case, however, there is still the requirement for a two part mix of which one part is hydrogen peroxide which to be stable must be maintained in a reasonably uncontaminated form and must be kept at acid pH's. Of course pH building substances must, therefore, necessarily be included in the activating component as the bleaching effect of peroxygen is only really significant in strongly alkaline environments.

If a suitable dry powder which upon mere water activation can be provided which will provide a significant degree of hair bleaching, other uses besides human hair bleaching becomes significant, for example, many methods of marking or identifying of animals are known. The traditional method has always been the use of heat branding. This results in a permanent marking which is hard to disguise making this a useful method of marking when there has been any tendency whatsoever to steal cattle etc. Such a method, however, has two main disadvantages. The first is that the pelt of the animal is permanently damaged. The second is the fact that owing to the pain that necessarily follows the application of such a hot brand or the like there is a period of, for example, one week following branding during which the animal gains no conditioning. This has severe economic ramifications when one considers the fact that for a vast number of animals annual marking is necessary. Other methods have been devised to overcome this. One that has lead to some degree of success has been the use of cryogenic techniques, for example, as exemplified in New Zealand Patent Specification No. 148055. Such a system itself results in some permanent damage to the pelt although to a lesser extent than that caused by heat branding. The marking obtained by such cryogenic branding is as a consequence of the growth of white hair corresponding to the area frozen. However for effective marking using this method it is necessary to prepare the surface of the skin to be treated i.e. by clipping or hair removal prior to the application of the brand. Moreover such cryogenic marking is permanent and would not have great application in areas where for example, it is necessary to mark animals annually as a consequence of some testing or draughting procedure. The most common form of marking that is used for this purpose is the use of paints, dyes or tags e.g. ear tags. Ear tags however can fall out or be torn out as well as leading to considerably difficulties in identification from a distance owing to the size of the actual tag. It is believed that if one wrong number is taken off a tag during the course of culling of a group of animals, significant time is lost in subsequently trying to find the incorrectly numbered animal and also in checking whether or not the actual animal had in fact been tested etc. Paints or the like are expensive or of limited effect in the sense that with long haired beasts the amount of material required is significant yet can still be rubbed off. There is therefore, some need to provide a system which will provide an effective and more economical method of marking which will overcome the above-mentioned difficulties. Such a method, it is believed, would involve the bleach marking of the hair of an animal. Normally the big moult of the year occurs in the spring. There is however, a secondary moult in autumn. One difficulty, however, with the application of a bleach to a long haired beast is the requirement that there be penetration of the bleaching composition to the base of the hair in order for an effective mark to be provided. Good penetration normally accompanies a low viscosity of the bleaching composition. This is not always desirable owing to the fact that there can be run off which prevents the use of such a free running composition in an effective manner to write numbers if numbers are required. Obviously some applications of the bleach marking composition would require the mere striping of an animal or the crossing of a pre-existing stripe so as to show for example, firstly that an animal has been tested and secondly that a test was negative or the animal had been treated. Obviously where numbers are required a brushable mix would be most appropriate although if, for example, a thixotropic mix without any large particle inclusion could be provided, a sprayable composition could be employed.

It becomes clear, therefore, if bleaching is to become a significant mode of animal marking, some stable, substantially foolproof means of generating an active peroxygen alkaline bleaching composition, preferably in the presence of an ammonia source, has to be provided. It is therefore, in this area that a one component water activated powder, in accordance with the present invention, would have wide spread application.

It is desirable, therefore, to have some consideration of the development that has occured over the years in regard to bleaching processes and powder components therefore. U.S. Pat. No. 1,894,277 which issued on the Jan. 17, 1933 relates to the discovery that certain peroxygen compounds can be used to enhance the bleaching effect of hydrogen peroxide. Hence, at that stage persulphate compounds were merely considered as an activating compound or a catalyst which enhances the bleaching effect of the hydrogen peroxide. U.S. Pat. No.

1,986,672 which issued on Jan. 1, 1935 to G. H. Bergman, relates to an early form of clothes washing detergent which would not bleach hair or fur adequately. It does, however, disclose the admixture of hydrogen peroxide and an anhydrous carbonate which the inventor stated—"It is my understanding that a percarbonate may be formed as a reaction product of the carbonate used and the hydrogen peroxide, but it may be that the hydrogen peroxide solution is merely mechanically or chemically bound to the carbonate in a manner analogous to water of hydration. My invention therefore relates to utilising hydrogen peroxide by incorporating it with an alkaline carbonate so as to form a compound that does not deteriorate when kept in closed containers and has bleaching properties not found in other commercial bleaches now on the market". This, therefore, evidences the recent development of the chemistry of peroxygen compounds.

U.S. Pat. No. 2,254,434 which issued on Sept. 2, 1941 to the Proctor and Gamble Company, relates to the creation of a new chemical which has a stabilizing effect on peroxygen compounds and evidences, therefore, the instability that is encountered with peroxygen compounds. U.S. Pat. No. 2,371,545 which issued on Mar. 13, 1945 to The Pennsylvania Salt Manufacturing Company relates to a means of adding a particular wetting agent to concentrated solutions of hydrogen peroxide to therefore make high and dangerous concentrations of hydrogen peroxide safe to handle when diluting for various manufacturing processes. Again, this evidences the instability of peroxygen compounds. U.S. Pat. No. 2,914,374 which issued Nov. 24, 1959 to Harris Research Laboratories Inc. relates to decolourising dead animal pelts for subsequent commercial use. It is interesting to note that at that particular time the available peroxygen compounds required an elevated temperature for effective bleaching. It is interesting to note also the virtual total reliance on hydrogen peroxide as the bleaching composition. U.S. Pat. No. 2,927,082 which issued Mar. 1, 1960 to E. I. du Pont de Nemours and Company relates to a hydrogen peroxide based strongly alkaline bleaching solution and again evidences the fact that almost total reliance for the bleaching was still being placed in the field of bleaching of cotton goods, wood pulps and the like on hydrogen peroxide. U.S. Pat. No. 3,193,464 issued July 6, 1965 to Sales Affilites Inc. deals with the difficulties of scalp irritation in bleaching processes and while relying on a two component mix relates to a bleach base which is in the form of various chemical soaps and includes an ammonia source compound for subsequent combination with a bleach booster which includes ammonium persulphate. Even so however, it becomes clear that a marketable one component system is not envisaged.

U.S. Pat. No. 2,991,228 issued July 4, 1961 to Lawrence Richard Bruce Incorporated, relates to powder compositions capable of being used in conjunction with aqueous hydrogen peroxide in order to not only form a paste with increased bleaching action for living hair but also deal with certain other difficulties that arise with the use of hydrogen peroxide. For its effect, however, the powder relies upon a phthalocyanine complex in conjunction with a mixture of magnesium salts. U.S. Pat. No. 3,337,466 issued Aug. 22, 1967 to Tintex Corporation, relates to a denture cleaner which would not have the power to produce an adequate commercial hair bleach. The bleach, however, contains potassium monopersulphate which is activated in aqueous alkaline solutions by certain other peroxygen compounds. As examples, ammonium persulphate and sodium carbonate peroxide are mentioned. This U.S. Patent therefore relates to the first unitary dry solid compositions known to us capable of self inducing a series of desired reactions upon simple addition to water. Various compositions disclosed in this specification, however, are of insufficient strength for the purpose of bleaching human hair or bleach marking animals and, further, in our view would not exhibit a significant shelf life, bearing in mind the various fillers disclosed. It is interesting to note that an ammonium peroxygen compound is being included in a dentifrice which in our view would leave undesirable after tastes. Since the "Composition A" disclosed therein relies upon a perborate compound we wonder, therefore, whether or not the enhanced activity resulting from a combination of a percarbonate and a persulphate is envisaged. Moreover U.S. Pat. No. 3,337,466 failed to appreciate the importance of various ions in the powder which can have an adverse effect on shelf life. Obviously shelf life is not going to be as critical with a dental cleanser as with a hair bleach, because while the same degree of bleaching will be required for hair, a denture which is simply soaked in a solution for a prolonged period, for example overnight, will always be accepted irrespective of the degree of bleaching thereof. U.S. Pat. No. 3,378,444 issued Apr. 16, 1968 to Rayette-Faberge Inc. deals with a two package system which is in our view a mere variant of pre-existing two component compositions. The dry powder component which is for mixture with hydrogen peroxide and a liquid ammonium soap to form a hair bleach of gelatinous consistency comprises a persulphate salt of a cation selected from the group consisting of alkali metals, ammonium and anhydrous alkali metal silicates, the silicated persulphate salt being present in a ratio range of about 1:4 to 1:7 and forming upon wetting with said liquids a gel in the pH range of about 9.3 to 10.0. Hence the composition really relates to a two component system which, however, appreciates the unexpected properties that can result from a correct accumulation of cations and anions within the various components. U.S. Pat. No. 3,651,209 issued Mar. 21, 1972 to F.M.C. Corporation, relates to a process of bleaching hair at substantially room temperatures with an aqueous solution of hydrogen peroxide or a compound yielding hydrogen peroxide in aqueous solution and either ammonium persulphate or an alkali metal persulphate in which the bleaching effectiveness of the above mixture is enhanced by adding either ammonium or an alkali metal peroxydiphosphate thereto. The disclosure, therefore, relates to the two components system which must be mixed more or less immediately prior to use, as they state—"In the make up of the bleaching solution the persulphate should be added just prior to utilising the bleaching solution for bleaching hair otherwise its activation effect is lost on standing or prolonged storage".

U.S. Pat. No. 3,651,931 issued Mar. 28, 1972 to The Gillette Company, relates to a package containing a two part hair or skin treating composition, the parts of which are intended to be mixed immediately before or during dispensing from the package, one part containing hydrogen peroxide and a buffer providing a pH of from 2.5 to 6.5 (to stablise presumably the hydrogen peroxide), the other part containing alkaline material, the relative amount of acid buffer and alkaline material being such that the pH of the final composition becomes from 7 to 12 immediately upon mixing so as to ensure bleaching by the hydrogen peroxide. This again is a specification which admits the instability of hydrogen peroxide in other than an acid environment and again evidences the fact that two component systems have and continue to be the main type of bleaching system.

U.S. Pat. No. 3,819,828 issued June 25, 1974 to the Proctor and Gamble Company, relates to an anhydrous water dispersible composition comprising a monopersulphate salt with an alkali metal cation, a compatible organic diluent, and a compatible alkaline buffering material to adjust the pH of aqueous solutions containing this composition to within the range of about 7 to about 11, said anhydrous composition desirably including a compatible surfactant selected from the group consisting of soaps and anionic, semi-polar, non-ionic, amphoteric and zwitterionic synethic surfactants. It is a composition as far as we have been able to determine which has not been successfully marketed. It is to be noted that the specification states—"The compositions of this invention depending upon the components can be used either as a shampoo or in combination with shampoos as cleaning and/or conditioning aids. Thus if there is a little surfactant present the compositions would normally be used after shampooing the hair as a creme rinse. On the other hand if there is a substantial amount of surfactant present the compositions of this invention can be used as shampoos or in combination with shampoos to clean the hair". The powder, therefore, is not a bleach with any degree of efficacy; and moreover while, it discloses a hair treating composition which for example, may include finely divided silica as a gelling agent and as a conditioning aid, it makes no disclosure of a unitary highly effective bleaching composition which will have in a closed environment a sustained shelf life.

U.S. Pat. No. 3,823,231 dated July 9, 1974 to F. P. Bucaria, relates to bleaching with a neutral pH and accordingly the emphasis in on a catalyst for bleaching at this pH range, namely, a thiocyanate catalyst. Again it relates to a two component mix which must be prepared shortly before use by quickly combining at least partially premixed portions. U.S. Pat. No. B 464,593 issued Mar. 9, 1976 to the Proctor and Gamble Company, relates to hair bleaching compositions containing arginine or various proteins or polypeptides having a arginine content, a peroxide compound and a bleaching accelerator as essential components. Again it relates to a two package system using a peroxide and a powder. Another object of the instant invention is to obtain an end product with a reduced ammonical odour. U.S. Pat. No. 3,961,635 issued June 8, 1976 to Henkel & Cie g.m.b.H. relates to a process and composition for bleaching hair containing oxidizing agents which liberate active oxygen and which contain keratose so as to reduce damage to the hair. Again it relates to a two component mixture. We have found that the thickeners suggested in the specification are not suitable as they tend to reduce the shelf life of the peroxygen compounds. Moreover we find it remarkable that there are suggestions to mix organics and inorganics of the nature mentioned in claim 4, such mixtures seriously affecting the shelf life especially in a one component mix. U.S. Pat. No. 4,096,240 issued June 20, 1978 to Lever Brothers Company, relates to a cosmetic composition for topical application to human skin for the purpose of skin lightening. It bears no similarity to a composition of the kind we envisage to be marketable as one component mix for bleaching animal or human hair. It relies to some extent on niacinamide or a precursor thereof.

British Pat. No. 859,276 granted to Unilever Limited, relates to a composition, as far as we have determined, which has never been successfully marketed. It relates to a powder composition which on mixture with water or aqueous hydrogen peroxide yields a bleaching composition suitable for application to the hair, the powder composition comprising a metallic peroxide of a kind as defined, a water soluble persulphate, ammonium bicarbonate and a water insoluble thickener. We have found that with metallic peroxides of the kind envisaged, for example sodium peroxide, explosive or potentially explosive compositions are provided.

During the course of an experiment based on those examples which include sodium peroxide, violent reactions resulted, and some compositions caught fire. It is interesting to note that on page 5 line 35 of British Pat. No. 859,276, there is a clear statement that metallic peroxides are preferable to percarbonates. In fact, page 8, line 5 appears to decry the use of a formula which includes a percarbonate. See also page 6, line 110. It is our belief, therefore, that none of the above mentioned specifications disclose a stable composition capable of being used for the bleaching of hair, whether animal or human, upon simple water activation. Therefore it should be realized that in the context of the current state of the art any water activatable powder composition which is nonexplosive in nature, has a sustained shelf life in acceptable containerized forms and which has a significant bleaching effect while unlikely to cause undue irritation to the skin of a person or the animal to which it is applied, will find widespread acceptance not only in the human hair bleaching market but also, as suggested earlier, in the farming community in connection with the bleach marking of animals.

BRIEF SUMMARY OF THE INVENTION

In one aspect, the present invention consists in a vapour proof enclosure, a marketable premixed dry bleaching powder capable, upon aqueous activation, of bleaching hair or keratinous fibre, said powder comprising at least 25% by weight of ammonium persulphate,
at least 25% by weight of a percarbonate compound selected from sodium percarbonate and potassium percarbonate, the ratio of ammonium persulphate to the percabonate compound being such as to provide, in the absence of other pH adjusting compounds, a pH in aqueous solution of from about 8.5 to about 11, and
pyrogenic silica, the powder having a total absence of any metal peroxide such as sodium peroxide.

Preferably the pyrogenic silica is present in a range of from 4 to 10%.

Preferably for those compositions which when activated are not to be sprayed a desiccant such as silica gel is included in addition to the pyrogenic silica.

Preferably the composition also includes a sequestering and/or wetting agent which is compatible with the shelf life and bleaching effect of the composition upon activation.

A further aspect of the present invention consists in a method of bleaching animal, including human, hair comprising the steps of taking from a vapour proof enclosure a quantity of a premixed dry bleaching powder capable upon aqueous activation of bleaching hair or keratinous fibre, said powder comprising at least 25% by weight of ammonium persulphate, at least 25% by weight of a percarbonate compound selected from sodium percarbonate and potassium percarbonate, the ratio of ammonium persulphate to the percarbonate compound being such as to provide, in the absence of other pH adjusting compounds, a pH in aqueous solution of from about 8.5 to about 11 and pyrogenic silica, the powder having a total absence of any metal peroxide such as sodium peroxide, mixing that quantity of powder with sufficient water as will provide an activated wet bleaching mix, and applying the wet bleaching mix while it remains active to the hair to be bleached.

In still a further aspect, the present invention consists in a method of preparing a dry bleaching powder capable upon aqueous activation of bleaching hair or keratinous fibre and which is capable of being marketed in a premixed form in a vapour proof enclosure, said powder comprising at least 25% by weight of ammonium persulphate, at least 25% by weight of a percarbonate compound selected from sodium percarbonate and potassium percarbonate, the ratio of ammonium persulphate to the percarbonate compound being such as to provide, in the absence of other pH adjusting compounds a pH in aqueous solution of from about 8.5 to about 11 and pyrogenic silica, the powder having a total absence of any metal peroxide such as sodium peroxide, said method comprising mixing the ammonium persulphate with a portion of the pyrogenic silica and mixing the percarbonate compound with the remaining portion of the pyrogenic silica and subsequently mixing the two separate dry mixes together.

Preferably at least one and preferably both of the persulphate and percarbonate compounds are present in a quantity greater than 35% by weight of the overall dry powder composition. Preferably the percarbonate is sodium percarbonate.

DETAILED DESCRIPTION OF THE PRESENT INVENTION

We have found that it is possible to prepare a strong bleaching powder which solely upon aqueous activation is effective in the bleaching of hair or keratinous fibre without unwanted side effects. It is thus suitable for use in hair salons and also in any marking regimen involving haired animals. In accordance with the present invention, the bleach is composed in powder form of at least 25% by weight of ammonium persulphate, and at least 25% by weight of a percarbonate compound selected from sodium percarbonate and potassium percarbonate, with the ratio of ammonium persulphate to the percarbonate compound being such as to provide in the absence of other pH adjusting compounds a pH in aqueous solution of from about 8.5 to about 11 and pyrogenic silica, the overall powder composition having a total absence of any unstable metal peroxide such as sodium peroxide. In the preferred form of the present invention the percarbonate compound is sodium percarbonate which is more readily available than potassium percarbonate. It is believed also that sodium percarbonate will give rise to a composition having a better shelf life than that of potassium percarbonate. Similarly ammonium persulphate is chosen over all other persulphates as it does not give rise to any unwanted metal ions which can, if present in significant quantities, lead to a reduced shelf life. Moreover by chosing ammonium persulphate not only is the alkaline pH obtained in solution but also a source of ammonia results which as can be determined from the prior art can enhance the bleaching properties.

As it is envisaged that the powder will be the sole bleaching agent, i.e. it would not ordinarily be admixed as with a two component system with a hydrogen peroxide system, higher percentages by weight of the oxidizing materials preferably ammonium persulphate and sodium percarbonate are present than has been the case with virtually all formulations hitherto known. Preferably at least 35% by weight of each component is present.

The presence of the pyrogenic silica or as it is sometimes known, flumed silica, is of significance and the inclusion should be at least in sufficient amounts as to not only act as a desiccant in the dry powder but also as a viscosity builder which will yield a thixotropic aqueous solution and also as a stabilising agent. This multiple effect resulting from the inclusion of the pyrogenic silica has not hitherto been considered. In the preferred method of formulation, the active oxidizing agents, the ammonium persulphate and the sodium percarbonate, are brought together only after each has been mixed with a portion of the pyrogenic silica. This ensures that each particle of the oxidizing compound is surrounded by very fine silica and consequently, when the two oxidizing agents are subsequently admixed, there is reduced particle to particle contact between the different oxidizing agents, thus, on a physical basis, enhancing the stability of the composition. Hence, the stability of the bleaching powder composition of the present invention results from the following:

(a) The choice of each oxidizing agent, preferably ammonium persulphate and sodium percarbonate.
(b) The packing of the same with pyrogenic silica which will tend to reduce particle to particle contact between the different oxidizing agents.
(c) The inclusion of pyrogenic silica as a desiccant which, when the powder is in a vapour proof enclosure, for example a sealed plastic container, an air-tight tin or the like, will ensure non-activation of the oxidizing agents by any trapped water vapour or the available water within the powder composition.
(d) The omission from the composition of any other metal peroxide, such metal peroxides in our view being unstable substances which should not be kept anywhere near the other components of the mix, contrary to what the prior art alleges.
(e) The omission of viscosity builders of the type which generate metal ions in solution (of which magnesium ions are believed to be a chief culprit) and give rise to instability and hence a reduction in shelf life when the powder is packed for shelf storage.
(f) The minimal inclusion of organic compounds which, as previously suggested, when mixed with peroxygen source materials, can lead to instability.

In some forms of the present invention, especially where the same is not sprayed, the desiccant effect of the pyrogenic silica can be enhanced by the inclusion of an additional desiccant, for example, silica gel, which again does not lead to any instability. Also, in order to enhance the solubility of the composition, a wetting agent which does not interfere significantly with the shelf life of the composition should be included. A suitable wetting agent, for example, would be selected from salts of N-lauryl beta-iminodipropionate (trade name Deriphat 160c) or a sodium salt of a sulphonated fatty acid, for example, sodium lauryl sulphate; obviously both would be included in a powder form.

It may also be desirable to include a sequestering agent and preferably ethylene diamine tetra acetic acid (EDTA) is chosen for this purpose.

From the foregoing it can be seen that the percentages of the various components can be varied. For example, while the pyrogenic silica is preferably in the range of from 4 to 10% it could in certain applications be increased, for example up to 20%.

Preferred forms of the powder will now be described.

A first form which is also suitable for spraying has the following composition:

Ammonium Persulphate: 35–60% by weight
Sodium Percarbonate: 35–50% by weight
Aerosil 200 (Pyrogenic Silica): 4–10% by weight
EDTA (sequestering agent): 0.5–2.5% by weight
Wetting Agent: 1–4% by weight In order to precoat the sodium percarbonate, half the total amount of pyrogenic silica and EDTA are mixed together with the total amount of the sodium percarbonate. The remainder of the pyrogenic silica and EDTA are mixed with the total amount of ammonium persulphate. These two premixes are then blended together and then thoroughly mixed. The wetting agent is finally added to the batch and only a short period of additional mixing is required so that the detergent is well dispersed throughout the mixture.

A composition which is suitable for human hair bleaching which would not normally to be sprayed is as follows:

Ammonium Persulphate: 35–50% by weight
Sodium Percarbonate: 35–50% by weight
Aerosil 200 (Pyrogenic Silica): 4–10% by weight
EDTA (sequestering agent): 0.5–2.5% by weight
Wetting Agent: 1–4% by weight
Microsized Amorphous Silica Gel: 0–8.5% by weight Much the same mixing procedure is employed. It is not critical whether the silica gel is distributed between the two mixtures prior to their final mixing together or not. The inclusion of a silica gel in the animal marking mix is permissible if it is unlikely that farmers are going to attempt to use the same as a spray.

The particle size of the various powder components is preferably such that a readily water soluble and/or dispersible composition results, for example, preferably the sodium percarbonate has a particle size of from about 800 to about 1000 microns.

Other trade sources for, for example, the pyrogenic silica include products such as Cabo-O-Sil M7 and Aerosil 200. Cabo-O-Sil M7 is a trade name of Cabot Corporation whereas Aerosil 200 is a trade name of Dugussa.

From the foregoing then it can be seen that the present invention provides a variety of dry powder bleaching compositions which provide effective bleaching solutions upon aqueous activation. Obviously if desired a humectant such as D-Glucitol could be incorporated in the final aqueous solution to ensure in an animal marking situation that the aqueous mix does not dry up prior to the bleaching effect taking place. Ideally however, such a humectant is not included in the dry bleach powder.

As previously suggested many different forms of packaging can be used. It is desirable, however, that the same be provided in vapour tight enclosures in order to ensure a prolonged shelf life, i.e. from the instance of manufacture of the mix through to the stage that the mix is activated. Obviously upon aqueous activation, especially at enhanced temperatures, the bleaching solution is only active for a short period i.e. a few hours at most. Thus, the sooner the activated mix is used after activation the better. This of course would always be the case in a human hair bleaching situation but care must be taken to ensure the same with regard to animal marking situations. Hence, again the need for a one component type mix as water is virtually always available. Often farmers, for example, will mistake the release of oxygen as being a sign of the efficacy of the solution. This is not always the case as such oxygen forms no real part in the bleaching operation and in fact the more violently oxygen is given off the less effective is the bleaching solution. However, such a release of oxygen does indicate the need to use freshly activated solutions. This is certainly the case with virtually all prior art compositions. It should be remembered throughout that the chemicals involved are very sensitive to contamination and to each other. For example, it is our belief that if potassium persulphate instead of ammonium persulphate was combined with sodium percarbonate, an explosive mix could very well result.

What is claimed is:

1. In a vapour proof enclosure, a marketable premixed dry bleaching powder capable upon aqueous activation of bleaching hair or keratinous fibre, said powder comprising at least 25% by weight of ammonium persulphate, at least 25% by weight of a percarbonate compound selected from sodium percarbonate and potassium percarbonate, the ratio of ammonium persulphate to the percarbonate compound being such as to provide in the absence of other pH adjusting compounds a pH in aqueous solution of from about 8.5 to about 11, and at least 4% by weight of pyrogenic silica.

2. A powder as claimed in claim 1 wherein the powder has been premixed by mixing said ammonium persulphate with a portion of the pyrogenic silica and mixing the percarbonate compound with the remaining portion of the pyrogenic silica prior to the whole composition being mixed together.

3. A powder as claimed in claim 1, wherein said pyrogenic silica is present in the range of from 4 to 10% by weight.

4. A powder as claimed in claim 1, wherein said percarbonate compound is sodium percarbonate.

5. A powder as claimed in claim 4, wherein there is at least 35% by weight of ammonium persulphate and at least 35% by weight of sodium percarbonate.

6. A powder as claimed in claim 1, wherein a desiccant form of silica gel is additionally included in the composition.

7. A powder as claimed in claim 6, wherein said silica gel is present in a microsized amorphous form and accounts for 0 to 8.5% by weight of the composition and the pyrogenic silica accounts for from 4 to 10% by weight of the composition.

8. A powder as claimed in claim 1, wherein a compatible sequestering agent is present.

9. A powder as claimed in claim 1, wherein a compatible wetting agent is included.

10. A powder as claimed in claim 1, having the composition as follows:

Ammonium persulphate: 35–60% by weight
Sodium percarbonate: 35–50% by weight
Pyrogenic silica: 4–10% by weight
EDTA: 0.5–2.5% by weight Compatible wetting agent: 1-4% by weight 11. A powder as claimed in claim 1 having the formula
Ammonium persulphate: 35-50% by weight
Sodium percarbonate: 35-50% by weight
Pyrogenic silica: 4-10% by weight
EDTA: 0.5-2.5% by weight
Compatible wetting agent: 1-4% by weight
Microsized amorphous silica gel: 0-8.5% by weight 12. A method of bleaching animal including human hair comprising the steps of
taking from a vapour proof enclosure a quantity of a premixed dry bleaching powder capable upon aqueous activation of bleaching hair or keratinous fibre, said powder comprising at least 25% by weight of ammonium persulphate, at least 25% by weight of a percarbonate compound selected from sodium percarbonate and potassium percarbonate, the ratio of ammonium persulphate to the percarbonate compound being such as to provide in the absence of other pH adjusting compounds a pH in aqueous solution of from about 8.5 to about 11 and at least 4% by weight of pyrogenic silica,
mixing that quantity of powder with sufficient water as will provide an activated wet bleaching mix, and
applying the wet bleaching mix while it remains active to the hair to be bleached.

13. A method of preparing a dry bleaching powder capable upon aqueous activation of bleaching hair or keratinous fibre and which is capable of being marketed in a premixed form in a vapour proof enclosure, said powder comprising at least 25% by weight of ammonium persulphate, at least 25% by weight of a percarbonate compound selected from sodium percarbonate and potassium percarbonate, the ratio of ammonium persulphate to the percarbonate compound being such as to provide in the absence of other pH adjusting compounds a pH in aqueous solution of from about 8.5 to about 11 and at least 4% by weight of pyrogenic silica, said method comprising mixing the ammonium persulphate with a portion of the pyrogenic silica and mixing the percarbonate compound with the remaining portion of the pyrogenic silica and subsequently mixing the two separate dry mixes together.

14. A method as claimed in claim 13 wherein the resulting dry bleaching powder has a composition of ammonium persulphate 35-60% by weight, sodium percarbonate 35-50% by weight, pyrogenic silica 4-10% by weight, EDTA 0.5-2.5% by weight, and compatible wetting agent 1-4% by weight and the EDTA is mixed in with at least one of the two separate dry mixes prior to their being mixed together, but the compatible wetting agent is only added after the two separate dry mixes have been mixed together.

15. A method as claimed in claim 14 wherein some of the EDTA is included in each of the two separate dry mixes prior to their being mixed together.

16. A method as claimed in claim 13 wherein the dry bleaching powder has a composition as claimed
Ammonium persulphate: 35-60% by weight
Sodium percarbonate: 35-50% by weight
Pyrogenic silica: 4-10% by weight
EDTA: 0.5-2.5% by weight
compatible wetting agent: 1-4% by weight
and the EDTA is mixed in with at least one of the two separate dry mixes prior to their being mixed together, but the compatible wetting agent is only added after the two separate dry mixes have been mixed together, the pyrogenic silica being included at any stage.

* * * * *